(12) United States Patent
Kwak et al.

(10) Patent No.: US 7,678,902 B2
(45) Date of Patent: Mar. 16, 2010

(54) PROCESS FOR THE PREPARATION OF 11-(4-[2-(2-HYDROXYETHOXY)ETHYL]-1-PIPERAZINYL)DIBENZO[B,F][1,4] THIAZEPINE

(75) Inventors: Byong-Sung Kwak, Daejeon (KR); Sang-Il Lee, Daejeon (KR); Hee-Jun Hwang, Daejeon (KR); Jong-Ho Lim, Daejeon (KR)

(73) Assignee: SK Holdings Co., Ltd., Seoul (KR)

( * ) Notice: Subject to any disclaimer, the term of this patent is extended or adjusted under 35 U.S.C. 154(b) by 752 days.

(21) Appl. No.: 11/571,116

(22) PCT Filed: Jun. 17, 2005

(86) PCT No.: PCT/KR2005/001866

§ 371 (c)(1),
(2), (4) Date: Dec. 21, 2006

(87) PCT Pub. No.: WO2006/001619

PCT Pub. Date: Jan. 5, 2006

(65) Prior Publication Data

US 2007/0225494 A1    Sep. 27, 2007

(30) Foreign Application Priority Data

Jun. 23, 2004    (KR)    ........................ 10-2004-0047128

(51) Int. Cl.
 C07D 417/04    (2006.01)
(52) U.S. Cl. .................................................... 540/551
(58) Field of Classification Search .................. 540/551
See application file for complete search history.

(56) References Cited

U.S. PATENT DOCUMENTS 4,879,288 A    11/1989    Warawa et al.
5,468,399 A    11/1995    Delfort et al.
5,646,297 A    7/1997    Canuti et al.
5,834,459 A    11/1998    Fu et al.

FOREIGN PATENT DOCUMENTS

| EP | 240228 A1 | 10/1987 |
| EP | 0282236 | 9/1988 |
| EP | 598646 A1 | 5/1994 |
| EP | 763774 A1 | 3/1997 |
| WO | WO-0155125 | 8/2001 |
| WO | WO-2004047722 | 6/2004 |

OTHER PUBLICATIONS

E. Cortes Cortes et. al., "Synthesis and Spectral Properties of Isomeric [(12-N-Methyl) and (10-N-methyl)] . . . ", Journal of Heterocyclic Chemistry, vol. 33, 1996, pp. 1723-1726, XP002510171.

*Primary Examiner*—Brenda L. Coleman
(74) *Attorney, Agent, or Firm*—Darby & Darby PC

(57) ABSTRACT

Disclosed is a process for the preparation of 11-(4-[2-(2-hydroxyethoxy)ethyl]-1-piperazinyl)-dibenzo[b,f][1,4]thiazepine. In the process, low-priced 2,2'-dithiosalicylic acid as starting material is subjected to bond formation reaction with 1-chloro-2-nitrobenzene in a basic aqueous solution, a nitro group reduction reaction is conducted, cyclization and chlorination reactions are simultaneously carried out in the presence of a equivalent amount of halogenating agent, a reaction with piperazine is continuously conducted without separation, and a reaction with 2-haloethoxyethanol is conducted, thereby it is possible to economically producing Quetiapine, that is, 11-(4-[2-(2-hydroxyethoxy)ethyl]-1-piperazinyl)-dibenzo[b,f][1,4]thiazepine, in an environmentally friendly manner. Particularly, the process is advantageous in that economic efficiency is assured because of use of the low-priced starting material, use of an organic solvent is minimized because a reaction is conducted in an aqueous solution, and it is possible to achieve the environmentally friendly and economical process having high commercial usefulness because the number of reaction steps of the process is reduced and because generation of acidic waste is minimized.

14 Claims, No Drawings

PROCESS FOR THE PREPARATION OF 11-(4-[2-(2-HYDROXYETHOXY)ETHYL]-1-PIPERAZINYL)DIBENZO[B,F][1,4]THIAZEPINE

This application is a national stage entry under 35 U.S.C. §371 of PCT/KR05/01866, filed Jun. 17, 2005.

TECHNICAL FIELD

The present invention relates to a process for the preparation of 11-4-[2-(2-hydroxyethoxy)ethyl]-1-piperazinyl)-dibenzo[b,f][1,4]thiazepine. More particularly, the present invention pertains to a process of economically, effectively, and commercially producing 11-(4-[2-(2-hydroxyethoxy)ethyl]-1-piperazinyl)-dibenzo[b,f][1,4]thiazepine in an environmentally friendly manner. In the process, 2,2'-dithiosalicylic acid, which is used as a raw material, is subjected to bond formation reaction with 1-chloro-2-nitrobenzene in a basic aqueous solution, a nitro group reduction reaction is conducted under a heterogeneous catalyst, cyclization and chlorination reactions are simultaneously carried out in the presence of a equivalent amount of halogenating agent and base, a reaction with piperazine is continuously conducted without separation, and a reaction with 2-haloethoxyethanol is conducted, so as to minimize the generation of acidic waste and the use of organic solvent.

BACKGROUND ART 11-(4-[2-(2-hydroxyethoxy)ethyl]-1-piperazinyl)-dibenzo[b,f][1,4]thiazepine, which is named Quetiapine, is an antipsychotic, and expressed by the following Formula 1.

Formula 1

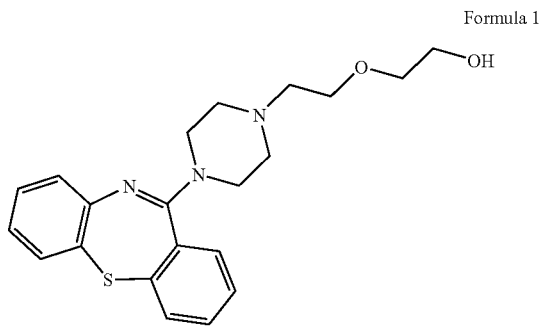

A representative process of producing 11-(4-[2-(2-hydroxyethoxy)ethyl]-1-piperazinyl)-dibenzo[b,f][1,4]thiazepine is as follows.

EP 240228 B1 discloses a production process in which 1-(2-hydroxyethoxy)ethylpiperazine reacts with an imino chloride compound expressed by the following Formula 2.

Formula 2

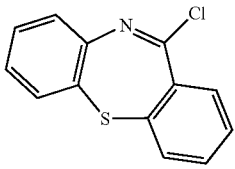

Meanwhile, the imino chloride compound, which is expressed by the above Formula 2, is produced by reacting 10H-dibenzo[b,f][1,4]thiazepine-11-on, which is expressed by the following Formula 3, with phosphorus oxychloride (POCl$_3$) (Helv. Chim Acta, 50, 245 (1967)).

Formula 3

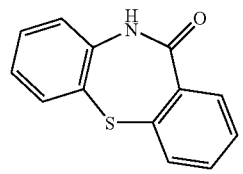

The 10H-dibenzo[b,f][1,4]thiazepine-11-on having the above Formula 3 is produced by reacting 2-aminodiphenyl sulfide reacts with phenylester chloroformate so as to produce phenyl 2-(phenylthio)phenyl carbamate, and then conducting a cyclization reaction in the presence of polyphosphoric acid.

However, in the above-mentioned production process, an excessive amount of polyphosphoric acid is used as a solvent, causing the generation of an excessive amount of acidic wastewater, resulting in harmful effects to the environment. Additionally, a lot of heat is generated when dilution is conducted using water in an end stage of the reaction, thus it is difficult to commercially produce it.

Furthermore, purification must be conducted using column chromatography in order to produce highly pure 11-(4-[2-(2-hydroxyethoxy)ethyl]-1-piperazinyl)-dibenzo[b,f][1,4]thiazepine of the above Formula 1, resulting in economic inefficiency.

As well, since the imino chloride compound of the above Formula 2 is unstable and is thus readily hydrolyzed due to moisture in air, there are many problems in the course of separating, purifying, and storing it. Particularly, in a commercial production process using a great amount of the compound, undesirably, hydrolyzed impurities are contained in final goods, thus reducing purity of the goods.

EP 282236 B1 discloses a method of producing 11-(4-[2-(2-hydroxyethoxy)ethyl]-1-piperazinyl)-dibenzo[b,f][1,4]thiazepine through a reaction of 11-piperazinyl-dibenzo[b,f][1,4]thiazepine of the following Formula 4 with 2-chloroethoxyethanol.

Formula 4

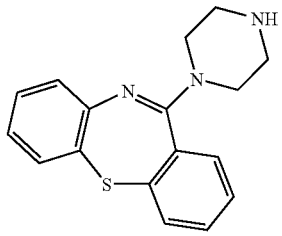

However, since the method employs the same intermediate as in the above-mentioned EP 240228 B1, it is disadvantageous in that it is difficult to achieve commercial production because of a lot of acidic wastewater generated by the use of an excessive amount of polyphosphoric acid and heat emission. Additionally, there are many problems in the method, for example, hydrolysis occurs due to cleavage of the unstable imino chloride compound of Formula 2.

According to WO 0155125, 2-aminodiphenyl sulfide reacts with phenylester chloroformate to produce phenyl 2-(phenylthio)phenyl carbamate, and N-[4-(2-chloroethyl) piperazine-1-aminodiphenyl sulfide is produced through a reaction using hydroxyethylpiperazine and another reaction using thionyl chloride. The resulting product, then, reacts with phosphorus oxychloride and phosphorus pentoxide to produce 11-[4-(2-chloroethyl)-1-piperazinyl]-dibenzo[b,f][1,4]thiazepine, and then reacts with ethylene glycol to produce 11-(4-[2-(2-hydroxyethoxy)ethyl]-1-piperazinyl)-dibenzo[b,f][1,4]thiazepine.

However, phosphorus oxychloride, which is used as a reaction solvent in the production method, generates a lot of acidic waste, and phosphorus pentoxide is difficult to handle because it is unstable in air and is highly corrosive and toxic, thus it is difficult to achieve commercial production. As well, sodium metal, which is used as a base in a reaction with ethylene glycol, is highly combustible and explosive, thus it is difficult to achieve commercial production.

DETAILED DESCRIPTION OF INVENTION

Technical Problem

The present inventors have conducted extensive studies to solve the above problems, resulting in the finding that it is possible to commercially produce Quetiapine using a low-priced compound as a starting material at high productivity in an economical and environmentally friendly manner, so as to minimize the generation of acidic waste and use of an organic solvent, and reduce the number of stages of a process, thereby accomplishing the present invention.

Accordingly, it is an object of the present invention to provide a process of commercially producing 11-(4-[2-(2-hydroxyethoxy)ethyl]-1-piperazinyl)-dibenzo[b,f][1,4]thiazepine in an economical, efficient and environmentally friendly manner, so as to minimize the generation of acidic waste and use of an organic solvent.

Technical Solution

In order to accomplish the above object, the present invention provides a process for the preparation of 11-(4-[2-(2-hydroxyethoxy)ethyl]-1-piperazinyl)-dibenzo[b,f][1,4]thiazepine expressed by the following Formula 1, comprising the following steps of:

(a) reacting 2,2'-dithiosalicylic acid which is expressed by Formula 5 with 1-chloro-2-nitrobenzene in a basic aqueous solution in the presence of or in the absence of a reducing agent, to produce 2-(2-nitrophenylthio)benzoic acid expressed by Formula 6;

(b) reducing a nitro group of 2-(2-nitrophenylthio)benzoic acid which is expressed by Formula 6 in the presence of hydrogen and a solvent under a heterogeneous metal catalyst, to produce 2-(2-aminophenylthio)benzoic acid expressed by Formula 7;

(c) simultaneously conducting cyclization and chlorination reactions of 2-(2-aminophenylthio)benzoic acid which is expressed by Formula 7 in an organic solvent in the presence of a halogenating agent and a base, and continuously reacting a resulting compound with piperazine without separation, to produce 11-piperazinyl-dibenzo[b,f][1,4]thiazepine expressed by Formula 4; and (d) reacting 11-piperazinyl-dibenzo[b,f][1,4]thiazepine which is expressed by Formula 4 with 2-haloethoxyethanol in an organic solvent under a base, to produce 11-(4-[2-(2-hydroxyethoxy)ethyl]-1-piperazinyl)-dibenzo[b,f][1,4]thiazepine expressed by Formula 1.

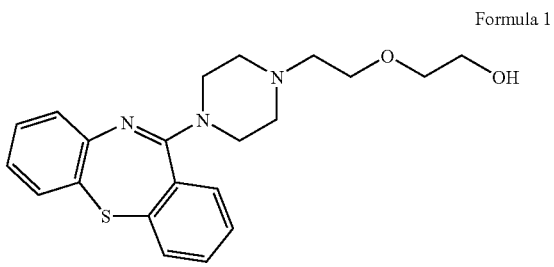

Formula 1

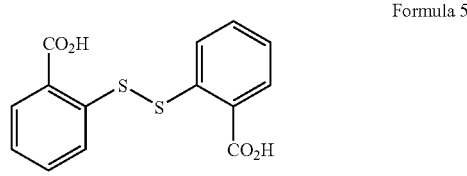

Formula 5

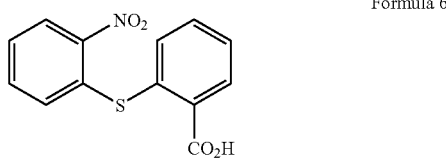

Formula 6

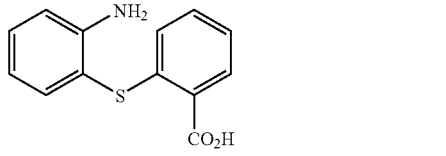

Formula 7

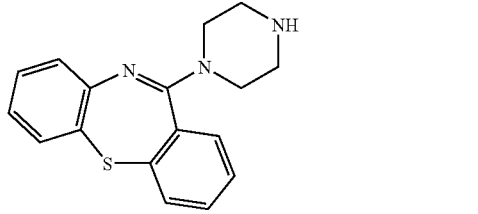

Formula 4

ADVANTAGEOUS EFFECTS

A process for the preparation of 11-(4-[2-(2-hydroxyethoxy)ethyl]-1-piperazinyl)-dibenzo[b,f][1,4]thiazepine according to the present invention is advantageous in that low-priced 2,2'-dithiosalicylic acid which is used as a starting material is subjected to bond formation reaction with 1-chloro-2-nitrobenzene in an aqueous solution and a nitro group reduction reaction is conducted under a heterogeneous catalyst so as to avoid the use of an unnecessary organic solvent, thus an economical and environmentally friendly process is assured. Furthermore, in subsequent processes, cyclization and chlorination reactions are simultaneously carried out in the presence of a equivalent amount of halogenating agent and base, and a reaction with piperazine is continuously conducted without separation and purification, so as to minimize generation of acidic waste and increase productivity, thereby problems of commercial production are effectively solved.

BEST MODE FOR CARRYING OUT THE INVENTION

A detailed description will be given of the present invention.

As described above, the present invention provides a process of economically, effectively, and commercially producing 11-(4-[2-(2-hydroxyethoxy)ethyl]-1-piperazinyl)-dibenzo[b,f][1,4]thiazepine in an environmentally friendly manner. In the process, low-priced 2,2'-dithiosalicylic acid which is used as raw material is subjected to bond formation reaction with 1-chloro-2-nitrobenzene in a basic aqueous solution, a nitro group reduction reaction is conducted under a heterogeneous catalyst, cyclization and chlorination reactions are simultaneously carried out in the presence of a equivalent amount of halogenating agent and base, a reaction with piperazine is continuously conducted without separation, and a reaction with 2-haloethoxyethanol is conducted, so as to minimize the generation of acidic waste and the use of an organic solvent.

According to the process of the present invention, first, 2,2'-dithiosalicylic acid, expressed by the above Formula 5, reacts with 1-chloro-2-nitrobenzene in a basic aqueous solution, to produce 2-(2-nitrophenylthio)benzoic acid, expressed by the above Formula 6.

The 1-chloro-2-nitrobenzene is used in the amount of 2-4 equivalents, and preferably, 2-2.5 equivalents, based on 1 equivalent of 2,2'-dithiosalicylic acid expressed by the above Formula 5. If the using amount of 1-chloro-2-nitrobenzene is less than 2 equivalents, the reaction does not proceed to completion, and, if the amount is more than 4 equivalents, the using amount is more than a necessary amount, resulting in economic inefficiency.

As the base of the basic aqueous solution, sodium hydroxide, potassium hydroxide, lithium hydroxide, sodium carbonate, potassium carbonate, or sodium bicarbonate, preferably sodium hydroxide or potassium hydroxide, and most preferably sodium hydroxide, is used. The using amount of base is 4-5 equivalents, and preferably, 4-4.5 equivalents based on 1 equivalent of 2,2'-dithiosalicylic acid. If the using amount of base is less than 4 equivalents, the conversion efficiency of the reaction is reduced, and, if the using amount of base is more than 5 equivalents, the using amount is more than necessary, resulting in economic inefficiency.

The reaction is carried out at a reaction temperature of 10-150° C., and preferably 80-110° C. If the reaction temperature is less than 10° C., the reaction rate is reduced, resulting in economic inefficiency.

Meanwhile, the reaction may be conducted either in the presence of or in the absence of the reducing agent. If a reducing agent is used, the reaction rate is increased and yield is improved. However, it may not be used. The reducing agent available in the present invention is exemplified by sodium borohydride, sodium hyposulfite, zinc, magnesium, or hydrazine, and preferably sodium borohydride or zinc.

Furthermore, if a phase transfer catalyst is used in the bond formation reaction, the reaction rate is tend to slightly increased. However, the increase is insignificant in comparison with when the catalyst is not used. Examples of a phase transfer catalyst useful in the present invention include benzyltrimethylammonium chloride, benzyltriethylammonium chloride, benzyltributylammonium chloride, tetramethylammonium chloride, tetraethylammonium chloride, tetrabutylammonium chloride, benzyltrimethylammonium bromide, benzyltriethylammonium bromide, benzyltributylammonium bromide, tetramethylammonium bromide, tetraethylammonium bromide, tetrabutylammonium bromide, benzyltrimethylammonium iodide, benzyltriethylammonium iodide, benzyltributylammonium iodide, tetramethylammonium iodide, tetraethylammonium iodide, tetrabutylammonium iodide, benzyltrimethylammonium sulfuric acid, benzyltriethylammonium sulfuric acid, benzyltributylammonium sulfuric acid, tetramethylammonium sulfuric acid, tetraethylammonium sulfuric acid, or tetrabutylammonium sulfuric acid, etc.

Next, 2-(2-nitrophenylthio)benzoic acid expressed by the above Formula 6 is subjected to a nitro group reduction reaction in the presence of hydrogen and a solvent under a heterogeneous metal catalyst, to produce 2-(2-aminophenylthio)benzoic acid expressed by the above Formula 7.

As the catalyst of the reduction (or hydrogenation) reaction, either metal itself or metal-impregnated support may be used.

The metal is selected from Raney-nickel (Raney-Ni), ruthenium (Ru), palladium (Pd), platinum (Pt), or rhodium (Rh), preferably Raney-nickel (Raney-Ni).

Examples of the available support include inorganic oxides, such as alumina, silica, zeolite, or molecular sieve.

The content of heterogeneous metal catalyst in the reactants of the reduction reaction is 2-30 wt %, and preferably 5-20 wt %. If the content of the metal catalyst is less than 2 wt %, the activity of the nitro group reduction reaction and selectivity of 2-(2-aminophenylthio)benzoic acid are reduced. If the content is more than 30 wt %, there is a disadvantage in that the economic efficiency of the process is reduced due to the high price of the metal.

The solvent suitable for the nitro group reduction reaction is exemplified by water ($H_2O$), methyl alcohol, ethyl alcohol, n-propyl alcohol, i-propyl alcohol, or a mixture thereof, and preferably water ($H_2O$) or methyl alcohol.

Meanwhile, a concentration of 2-(2-nitrophenylthio)benzoic acid in the reactants is maintained at 1-50 wt %, and preferably 10-40 wt %. If the concentration is less than 1 wt %, productivity is reduced because the solvent is used in an excessive amount. If the concentration is more than 50 wt %, there is a disadvantage in that reactivity is reduced.

Furthermore, in the nitro group reduction reaction, the reaction pressure is 10-1000 psig, and preferably 100-900 psig. The reaction temperature is 1-200 t, and preferably 10-170° C. The reaction time is preferably 1-14 hours.

Next, 2-(2-aminophenylthio)benzoic acid which is expressed by the above Formula 7 is simultaneously subjected to cyclization and chlorination reactions in the presence of a equivalent amount of halogenating agent and base in an organic solvent, and then reacted with piperazine without separation, to produce 11-piperazinyl-dibenzo[b,f][1,4]thiazepine expressed by the above Formula 4.

The halogenating agent which is available in the present invention is phosphorus oxychloride ($POCl_3$) or thionyl chloride ($SOCl_2$), and preferably phosphorus oxychloride. The use of thionyl chloride is problematic in that conversion efficiency is poor in the chlorination reaction even though the cyclization reaction is preferably processed. The halogenating agent is used in the amount of 2.0-4.0 equivalents, and preferably 2.0-2.5 equivalents, based on 1 equivalent of 2-(2-aminophenylthio)benzoic acid expressed by the above Formula 7. If the using amount of halogenating agent is less than 2.0 equivalents, the reaction does not proceed to completion, and, if the amount is more than 4.0 equivalents, the using amount is more than necessary, resulting in economic inefficiency.

The base which is available in the cyclization and chlorination reactions is dimethyl aniline, pyridine, or triethyl amine, etc., and preferably dimethyl aniline. The base is used in the amount of 0.1-2.0 equivalents, and preferably 0.6-1.5 equivalents, based on 1 equivalent of 2-(2-aminophenylthio) benzoic acid. If the using amount of base is less than 0.1 equivalents, conversion efficiency of the reaction is reduced, and, if the amount is more than 2.0 equivalents, the using amount is more than necessary, resulting in economic inefficiency.

A reaction temperature in the cyclization and chlorination reactions is 10-150° C., and preferably 80-110° C. If the reaction temperature is lower than 10° C., a reaction rate is reduced, and, if the reaction temperature is higher than 150° C., generation of impurities is increased, resulting in economic inefficiency.

The organic solvent which is available in the cyclization and chlorination reactions is acetonitrile, ethyl acetate, benzene, toluene, xylene, or a mixture thereof, and preferably toluene or xylene.

Meanwhile, the piperazine is used in the amount of 1.0-5.0 equivalents, and preferably 2.0-3.5 equivalents, based on 1 equivalent of 2-(2-aminophenylthio)benzoic acid expressed by the above Formula 7. If the using amount of piperazine is less than 1.0 equivalent, conversion efficiency of the reaction is reduced and selectivity is reduced due to a side reaction. If the amount is more than 5.0 equivalents, the amount used is more than necessary, resulting in economic inefficiency.

The temperature of the reaction with piperazine is 10-150° C., and preferably 90-120° C. If the reaction temperature is lower than 10° C., the reaction rate is reduced, resulting in inefficiency.

Finally, 11-piperazinyl-dibenzo[b,f][1,4]thiazepine which is expressed by the above Formula 4 reacts with 2-haloethoxyethanol in an organic solvent under a base, to produce 11-(4-[2-(2-hydroxyethoxy)ethyl]-1-piperazinyl)-dibenzo[b,f][1,4]thiazepine expressed by the above Formula 1.

2-haloethoxyethanol is exemplified by 2-chloroethoxyethanol, 2-bromoethoxyethanol, or 2-iodoethoxyethanol, and preferably 2-chloroethoxyethanol.

The reaction at the last step is not limited, but may be conducted according to a technology known in the art. Preferably, the reaction is conducted under the following conditions.

The base available in the reaction is exemplified by sodium carbonate or potassium carbonate, and a reaction solvent is exemplified by an aromatic solvent, such as benzene or toluene, etc., an alcohol solvent, such as methanol, ethanol, propanol, etc., or butanol, dimethyl formamide, N-methylpyrrolidone, or a mixture thereof, and preferably a mixed solvent of N-methylpyrrolidone and propanol.

Furthermore, alkaline metal halide may be used as a catalyst, and the most effective catalyst is sodium iodide. When sodium iodide is used in a required amount of catalyst, halogen of 2-haloethoxyethanol is substituted by iodine, resulting in an increase in the reaction rate.

Meanwhile, the reaction temperature ranges from room temperature to a temperature that corresponds to a reflux condition of the mixed solvent, and is preferably the temperature that corresponds to the reflux condition of the mixed solvent. The reaction time is 15-30 hours, and preferably 24 hours.

As described above, in the process according to the present invention, low-priced 2,2'-dithiosalicylic acid is reacted with 1-chloro-2-nitrobenzene in a basic aqueous solution, and the nitro group reduction reaction is subsequently conducted using the heterogeneous catalyst in the same aqueous solution so as to avoid the use of an unnecessary organic solvent, thereby an economical and environmentally friendly process is assured. Furthermore, 2-(2-aminophenylthio)benzoic acid which is obtained in the nitro group reduction reaction is subjected to cyclization and chlorination reactions in the presence of a equivalent amount of halogenating agent and base, and a reaction with piperazine is continuously conducted without separation, so as to minimize the generation of acidic waste and use of an organic solvent, thereby it is possible to assure an environmentally friendly process and avoid economic inefficiency. As well, it is possible to conduct commercial production and improve commercial productivity by reducing the number of steps of the process.

MODE FOR CARRYING OUT THE INVENTION

Having generally described this invention, a further understanding can be obtained by reference to specific examples which are provided herein for purposes of illustration only and are not intended to be limiting unless otherwise specified.

Example 1 a) Production of 2-(2-nitrophenylthio)benzoic acid 2,2'-dithiosalicylic acid (45.7 g, 0.15 mol) and sodium hydroxide (24.5 g, 0.61 mol) were put in a 0.5 L reactor having an agitator and a reflux device, and dissolved in 160 ml of water. Zinc (9.8 g) was added thereto, and a reaction was conducted at 40° C. for 1 hour. 1-chloro-2-nitrobenzene (48.2 g, 0.31 mol) was added thereto, and the resulting mixture was refluxed for 6 hours and extracted with toluene (200 ml×2) to remove unreacted 1-chloro-2-nitrobenzene so as to produce a 2-(2-nitrophenylthio)benzoic acid aqueous solution.

b) Production of 2-(2-aminophenylthio)benzoic acid

Raney-nickel (16.7 g) and 87 ml of water were added to the 2-(2-nitrophenylthio)benzoic acid aqueous solution which was obtained in step a), and a reaction was conducted at a hydrogen pressure of 450 psi and a reaction temperature of 110° C. for 3 hours. The reactant was cooled to room temperature, and the metal catalyst was filtered and thus removed. The filtrate was neutralized with a hydrochloric acid aqueous solution, solids were filtered out, and drying was conducted at reduced pressure, to produce 2-(2-aminophenylthio)benzoic acid hydrochloride (55 g).

c) Production of 11-piperazinyl-dibenzo[b,f][1,4]thiazepine 2-(2-aminophenylthio)benzoic acid (50 g) which was obtained in step b) was suspended in toluene (216 ml) in a 0.5 L reactor having an agitator and a reflux device, phosphorus oxychloride (27.3 g) was added thereto, and a reaction was conducted at 90° C. for 2 hours. The removal of starting material was confirmed using HPLC, additional dimethyl aniline (21.5 g) and phosphorus oxychloride (28.6 g) were added thereto, and reflux was conducted for 2 hours. The reactants were cooled to room temperature, and washed with water (160 ml).

Piperazine (53.6 g) was added to the resulting toluene solution, reflux was conducted for 1 hour, and the resulting solution was cooled to room temperature. Washing was carried out with water (125 ml×3) to remove remaining piperazine, and an organic layer was vacuum distilled to produce oil. The oil was dissolved in ethanol, and a hydrochloric acid-ethanol solution was added thereto, to produce 11-piperazinyl-dibenzo[b,f][1,4]thiazepine hydrochloride (46.4 g).

d) Production of 11-[4-[2-(hydroxyethoxy)ethyl]-1-piperazinyl]-dibenzo[b,f][1,4]thiazepine 11-piperazinyl-dibenzo[b,f][1,4]thiazepine hydrochloride (40 g) obtained in step c), sodium carbonate (69.3 g), sodium iodide (0.65 g), and 2-chloroethoxyethanol (14.7 g) were added to a solution of n-propyl alcohol (260 ml) and N-methylpyrrolidone (65 ml), and reflux was conducted for 24 hours. Ethyl acetate (327 ml) was added thereto, washing was conducted using water (2×1000 ml), an organic layer was separated to be dried with magnesium sulfate, and a solvent was removed at reduced pressure, thereby oil was created. The resulting oil was completely dissolved in ethanol, and fumaric acid (7.1 g) was added thereto, to produce 11-[4-[2-(hydroxyethoxy)ethyl]-1-piperazinyl]-dibenzo[b,f][1,4]thiazepine fumarate (34 g).

The invention claimed is:

1. A process for the preparation of 11-(4-[2-(2-hydroxyethoxy)ethyl]-1-piperazinyl)-dibenzo[b,f][1,4]thiazepine expressed by Formula 1, comprising the following steps of:
(a) reacting 2,2'-dithiosalicylic acid which is expressed by Formula 5 with 1-chloro-2-nitrobenzene in a basic aqueous solution in the presence of or in the absence of a reducing agent, to produce 2-(2-nitrophenylthio)benzoic acid expressed by Formula 6;
(b) reducing a nitro group of 2-(2-nitrophenylthio)benzoic acid which is expressed by Formula 6 in the presence of hydrogen and a solvent under a heterogeneous metal catalyst, to produce 2-(2-aminophenylthio)benzoic acid expressed by Formula 7;
(c) simultaneously conducting cyclization and chlorination reactions of 2-(2-aminophenylthio)benzoic acid which is expressed by Formula 7 in an organic solvent in the presence of a halogenating agent and a base, and continuously reacting a resulting compound with piperazine without separation, to produce 11-piperazinyl-dibenzo[b,f][1,4]thiazepine expressed by Formula 4; and
(d) reacting 11-piperazinyl-dibenzo[b,f][1,4]thiazepine which is expressed by Formula 4 with 2-haloethoxyethanol in an organic solvent under a base, to produce 11-(4-[2-(2-hydroxyethoxy)ethyl]-1-piperazinyl)-dibenzo[b,f][1,4]thiazepine expressed by Formula 1

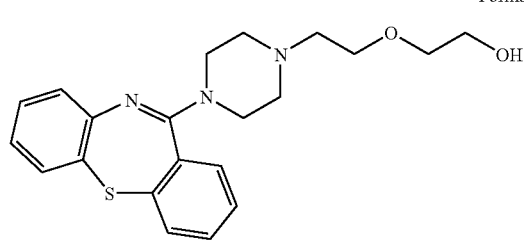

Formula 1

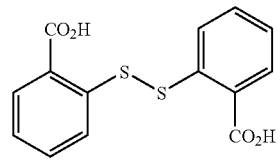

Formula 5

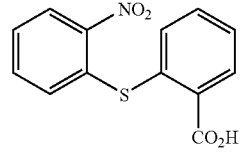

Formula 6

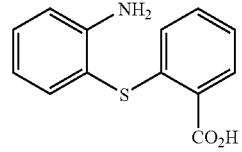

Formula 7

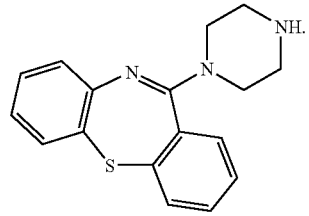

Formula 4

2. The process as set forth in claim 1, wherein, in the step (a), a reaction temperature is 10-150° C., and the 1-chloro-2-nitrobenzene is used in the amount of 2-4 equivalents of based on 1 equivalent of 2,2'-dithiosalicylic acid.

3. The process as set forth in claim 1, wherein, in the step (a), the base of the basic aqueous solution is sodium hydroxide, potassium hydroxide, lithium hydroxide, sodium carbonate, potassium carbonate, or sodium bicarbonate, and the base is used in the amount of 4-5 equivalents based on 1 equivalent of 2,2'-dithiosalicylic acid.

4. The process as set forth in claim 1, wherein, in the step (a), the reducing agent is sodium borohydride, sodium hyposulfite, zinc, magnesium, or hydrazine.

5. The process as set forth in claim 1, wherein, in the step (b), a reaction pressure is 10-1000 psig, a reaction temperature is 1-200° C., and a reaction time is 1-14 hours.

6. The process as set forth in claim 1, wherein, in the step (b), a content of 2-(2-nitrophenylthio)benzoic acid in reactants is 1-50 wt %.

7. The process as set forth in claim 1, wherein, in the step (b), the solvent is water, methyl alcohol, ethyl alcohol, n-propyl alcohol, i-propyl alcohol, or a mixture thereof.

8. The process as set forth in claim 1, wherein, in the step (b), the heterogeneous metal catalyst is selected from a group consisting of Raney-nickel (Raney-Ni), ruthenium (Ru), palladium (Pd), platinum (Pt), and rhodium (Rh), and a content of heterogeneous metal catalyst in reactants is 2-30 wt %.

9. The process as set forth in claim 1, wherein, in the step (b), the heterogeneous metal catalyst is produced by impregnating at least one support selected from a group consisting of alumina, silica, zeolite and molecular sieve, with at least one metal selected from a group consisting of Raney-nickel, ruthenium, palladium, platinum and rhodium, and a content of heterogeneous metal catalyst in reactants is 2-30 wt %.

10. The process as set forth in claim 1, wherein, in the step (c), a reaction temperature is 10-150° C. in the cyclization and chlorination reactions, and the halogenating agent is used in the amount of 2.0-4.0 equivalents and the base is used in the amount of 0.1-2.0 equivalents, based on 1 equivalent of 2-(2-aminophenylthio)benzoic acid.

11. The process as set forth in claim 1, wherein, in the step (c), a reaction temperature is 10-150° C. in the reaction with piperazine, and the piperazine is used in the amount of 1.0-5.0 equivalents based on 1 equivalent of 2-(2-aminophenylthio) benzoic acid.

12. The process as set forth in claim 1, wherein, in the step (c), the halogenating agent is phosphorus oxychloride ($POCl_3$) or thionyl chloride ($SOCl_2$).

13. The process as set forth in claim 1, wherein, in the step (c), the base is dimethyl aniline, pyridine, or trimethyl amine.

14. The process as set forth in claim 1, wherein, in the step (c), the organic solvent is acetonitrile, ethyl acetate, benzene, toluene, xylene, or a mixture thereof.

* * * * *